| United States Patent [19] | [11] Patent Number: 5,037,996 |
|---|---|
| Suzuki et al. | [45] Date of Patent: Aug. 6, 1991 |

[54] PROCESS FOR PRODUCING 1,4-BUTANEDIOL

[75] Inventors: Sadakatsu Suzuki; Hiroyuki Inagaki; Hiroshi Ueno, all of Saitama, Japan

[73] Assignee: Tonen Corporation, Tokyo, Japan

[21] Appl. No.: 554,099

[22] Filed: Jul. 16, 1990

Related U.S. Application Data

[63] Continuation of Ser. No. 450,092, Dec. 13, 1989, abandoned.

[30] Foreign Application Priority Data

Dec. 14, 1988 [JP] Japan ............................... 63-313759

[51] Int. Cl.$^5$ ..................... C07C 29/136; C07C 31/20
[52] U.S. Cl. .................................................. 568/864
[58] Field of Search ......................................... 568/864

[56] References Cited

U.S. PATENT DOCUMENTS

| 2,322,099 | 6/1943 | Schmidt | 568/864 |
| 3,432,560 | 3/1969 | Martin et al. | 568/864 |
| 3,478,112 | 11/1969 | Adam et al. | 568/864 |
| 3,770,837 | 11/1973 | Farstritsky et al. | 568/864 |
| 3,855,319 | 12/1974 | Hobbs et al. | 568/864 |
| 4,010,197 | 3/1977 | Toriya et al. | 568/864 |
| 4,032,458 | 6/1977 | Cooley et al. | 568/864 |
| 4,048,196 | 9/1977 | Broecker et al. | 568/864 |
| 4,550,185 | 10/1985 | Mabry et al. | 568/864 |
| 4,827,001 | 5/1989 | Attig et al. | 568/864 |

FOREIGN PATENT DOCUMENTS

| 44-32567 | 12/1969 | Japan . |
| 47-23294 | 6/1972 | Japan . |
| 63-88044 | 4/1988 | Japan . |
| 02-25434 | 1/1990 | Japan . |
| 1551741 | 8/1979 | United Kingdom . |

*Primary Examiner*—J. E. Evans
*Attorney, Agent, or Firm*—E. F. Sherer

[57] ABSTRACT

A process of producing 1,4-butanediol by catalytically hydrogenating maleic acid anhydride and/or succinic acid anhydride in a gas phase and in the presence of a catalyst.

4 Claims, No Drawings

PROCESS FOR PRODUCING 1,4-BUTANEDIOL

This is a continuation of application Ser. No. 450,092 filed Dec. 13, 1989, now abandoned.

BACKGROUND OF THE INVENTION

The present invention relates to a process for producing 1,4-butanediol and, more in particular, it relates to a process for producing 1,4-butanediol, in which maleic acid anhydride and/or succinic acid anhydride are catalytically hydrogenated in a gas phase under the presence of a catalyst.

1,4-butanediol is a compound useful as starting material for polybutylene terephthalate resin, polyurethane resin, etc. Accordingly, there is a need for a process for producing 1,4-butanediol at reduced cost and increased efficiency.

The following processes for producing γ-butyrolactone or 1,4-butanediol by catalytic hydrogenation of maleic acid anhydride and/or succinic acid anhydride or derivatives thereof have been disclosed.

(i) A process for producing γ-butyrolactone in which maleic acid anhydride or succinic acid anhydride, etc. are catalytically hydrogenated in a gas phase by using a catalyst comprising zinc-copper-chromium (Japanese Patent Publication Sho 44-32567).

(ii) A process for producing γ-butyrolactone in which maleic acid anhydride and/or succinic acid anhydride, etc. are catalytically hydrogenated in a gas phase under the presence of a reduction catalyst comprising copper oxide-beryllium oxide-zinc oxide (Japanese Patent Publication Sho 47-23294).

(iii) A process for producing γ-butyrolactone in which maleic acid anhydride or succinic acid anhydride is hydrogenated in a liquid phase under the presence of a catalyst comprising nickel-molybdenum-barium and rhenium carried on a support Japanese Patent Laid-Open Sho 63-88044).

(iv) A process for producing 1,4-butanediol in which maleic acid anhydride and/or succinic acid anhydride, etc. are hydrogenated in a liquid phase under the presence of a catalyst containing elements belonging to sub-VII and sub-VIII groups or compounds thereof (Japanese Patent Laid-Open Sho 51-133212).

(v) A process for producing 1,4-butanediol in which maleic acid diester or fumaric acid diester, etc. are hydrogenatively decomposed in a gas phase in the presence of a copper chromite catalyst oxide-zinc oxide catalyst (Japanese Patent Application Sho 63-175062).

The processes of producing 1,4-butanediol which are disclosed above have a number of problems. For instance, in a process of catalytically hydrogenating maleic acid anhydride and/or succinic acid anhydride in a gas phase under the presence of a catalyst, many times only γ-butyrolactone is formed instead of the desired 1,4-butanediol, except for the process proposed above by the present inventors. Further, the method of hydrogenating maleic acid anhydride and/or maleic acid in a liquid phase under the presence of a catalyst has a problem of requiring a high pressure of about 200 kg/cm$^2$ and, thus requires an enormous installation cost and running cost. Further, although a process of hydrogenatively decomposing maleic acid diester, etc. in a gas phase under the presence of a catalyst does not require the high pressure described above, it still requires a step of diesterifying maleic acid anhydride, which makes the process extremely complicated. That is, since the reaction of converting a monoester into a diester is a equilibrium reaction, two reaction steps are required for sufficiently completing the reaction and it is necessary to add three reaction steps including the mono-esterifying step.

Further, a process for producing 1,4-butanediol by catalytic hydrogenation of maleic acid anhydride and/or succinic acid anhydride in a gas phase has not yet been known.

The present invention overcomes or at least mitigates the above-described problems of high installation cost and running cost and complicated processes for producing 1,4-butanediol from maleic acid anhydride and/or succinic acid anhydride.

DESCRIPTION OF THE INVENTION

The present inventors have found that it will be beneficial if maleic acid anhydride and/or succinic acid anhydride are hydrogentated directly at a reduced pressure thereby producing 1,4-butanediol not by way of diesters and have made various studies on gas phase hydrogenation processes.

It has also been found that the γ-butyrolactone can only be obtained in the gas phase hydrogenation of maleic acid anhydride and/or succinic acid anhydride, because the reaction is conducted at a low hydrogen/starting material ratio and at a pressure near the normal pressure in each of the cases. Then, when a hydrogenating reaction has been carried out at a higher hydrogen/starting material ratio than usual and under an elevated pressure within such a range that the gas phase can be maintained, it has been found that 1,4-butanediol can be produced at a high yield and the present invention has been accomplished based on such a finding.

That is, the present invention concerns a process for producing 1,4-butanediol by catalytically hydrogenating maleic acid anhydride and/or succinic acid anhydride, wherein reaction is conducted in a gas phase under the presence of a solid catalyst containing rhenium, copper and zinc.

Catalyst

The catalyst used in the present invention is usually a previously reduced rhenium oxide-copper oxide-zinc oxide catalyst. Such a catalyst is prepared, for example, by mixing an aqueous solution of a copper compound, for example, an aqueous solution of copper sulfate or copper nitrate with an aqueous solution of sodium hydroxide, adding zinc oxide, stirring sufficiently, recovering by filtration and, after drying and pulverization step, molding them into a predetermined shape by using a molding machine, mixing an acetone solution of rhenium oxide to the molding product, evaporizing acetone and then applying a drying step. In this preparation method, a catalyst with support can be obtained in which rhenium oxide and copper oxide are supported on zinc oxide.

Reduction of the catalyst in the present invention is carried out, for example, by passing a nitrogen gas containing 2 vol % of hydrogen to a catalyst at a gas space velocity converted into that at normal temperature and normal pressure (hereinafter simply referred to as G.H.S.V., which shows a value for normal temperature and normal pressure in each of the cases) at about 2,400 hr$^{-1}$ and a pressure of several tens of kg/cm$^2$G at 170° C. for one day and one night, further gradually increasing the hydrogen concentration to 100 vol % and then passing the gas for several hours at a temperature of the catalyst bed of 200° C.

Solvent

Although there is no particular restrictions for the solvent usable in the present invention, γ-butyrolactone, tetrahydrofuran, dimethyl ether, diethyl ether and 1,4-dioxane may be used for example. Among them, γ-butyrolactone is particularly preferred since it is a good solvent for maleic acid anhydride and succinic acid anhydride, one of hydrogenation products and considered to be an intermediate product of 1,4-butanediol. The solvent does not need be used.

Catalytic Condition

Catalytic contact between a gas mixture of maleic acid anhydride and/or succinic acid anhydride and a hydrogen and a catalyst can properly be selected from the methods known so far. For instance, such methods include contacting the gas mixture and the catalyst in a fixed bed system, a method of contacting them in a moving bed system or a method of contacting them in a fluidized bed system. Depending on a case, the gas mixture and the catalyst can be brought into contact batchwise.

The time of contact between the gas mixture of maleic acid anhydride and/or succinic acid anhydride and hydrogen, and the catalyst is from 1,000 to 100,000 $hr^{-1}$, preferably, about 4,000 to 20,000 $hr^{-1}$ expressed as G.H.S.V.

The reaction temperature in the present invention is about 180° to 280° C., the reaction pressure is about 10 to 100 $kg/cm^2G$ and the molar ratio of hydrogen gas to maleic acid anhydride and/or succinic acid anhydride is about from 100 to 1,500. The reaction temperature, the reaction pressure and the hydrogen gas/starting material molar ratio are property selected within such a range as capable of maintaining the gas phase.

However, if the hydrogen gas/starting material molar ratio is below 100, it tends to cause reduction in the reaction rate and catalyst degradation due to the formation of carbonaceous substance. On the other hand, if it exceeds 1,500, since a great amount of hydrogen has to be recycled, it is disadvantageous from an economical point of view.

By the process according to the present invention, it is possible to obtain 1,4-butanediol from maleic acid anhydride and/or succinic acid anhydride in one step reaction at a high yield, as well as to remarkably simplify the production process since the diesterifying step for maleic acid anhydride and/or succinic acid anhydride is saved. In addition, as compared with hydrogenation in liquid phase, since 1,4-butanediol can be produced at a remarkably lower pressure, there can be obtained a effect of reducing the installation cost and the running cost.

The present invention will now be described referring to examples but the invention is not restricted only to these examples.

EXAMPLE 1

Into a solution containing 9.63 g of rhenium oxide ($Re_2O_7$) dissolved in one liter of acetone, 512.5 g of a commercially available catalyst with the copper oxide/zinc oxide weight ratio of 50/45 (trade name: N-211, manufactured by Nikki Kagaku Co.) was added and, while stirring properly left at a room temperature for one day and one night. Then, it was heated at 80° C. to evaporate and dry-up acetone and then further dried in a drier at 120° C. for 12 hours and 150° C. for 12 hours to prepare a rhenium oxide-copper oxide-zinc catalyst. The rhenium content in the resultant catalyst, as a metal component, was 1.5% by weight.

15 cc of the catalyst prepared as described above was charged into a fixed bed reactor (15 mm × 600 mm) and pressurized in a nitrogen gas stream to 15 $kg/cm^2G$ and heated to 170° C. Subsequently, hydrogen was gradually added to the nitrogen gas stream and nitrogen gas containing 2 vol % of hydrogen was caused to pass under 15 $kg/cm^2G$, at 170° C., and G.H.S.V. of 2,400 $hr^{-1}$ over one night. Then, hydrogen concentration was gradually increased up to 100% by volume hydrogen while taking care such that the catalyst bed temperature did not exceed 200° C., and reduction was conducted under 15 $kg/cm^2G$, at 200° C. and at G.H.S.V. of 2,400 $hr^{-1}$ for two hours. The product was analyzed by gas chromatography and the product was identified by GC-MS.

As a result, conversion of maleic acid anhydride was 100 mol %, and 40.8 mol % of 1,4-butanediol and 17.5 mol % of tetrahydrofuran were formed based on maleic acid anhydride supplied. Other products were γ-butyrolactone, n-butanol, n-propanol, etc. Succinic acid anhydride was not detected in the product.

EXAMPLE 2

The catalyst preparation, the reduction treatment and the 1,4-butanediol production were conducted in the same procedures as those in Example 1 except for changing the pressure upon catalyst reduction and the reaction pressure to 40 $kg/cm^2G$ and the reaction temperature to 200° C. and changing the molar ratio of maleic acid anhydride to γ-butyrolactone to 1/1 and G.H.S.V. to 9,000 $hr^{-1}$.

As a result, the conversion of maleic acid anhydride was 100 mol %, and 94.3 mol % of 1,4-butanediol and 3.3 mol % of tetrahydrofuran were formed based on maleic acid anhydride supplied. Succinic acid anhydride was not detected in the product.

EXAMPLE 3

The catalyst preparation, the reduction treatment and the 1,4-butanediol production were conducted in the same procedures as those in Example 1 except for replacing maleic acid anhydride with succinic acid anhydride and changing the molar ratio of succinic acid anhydride to γ-butyrolactone to 1/4.

As a result, the conversion of the succinic acid anhydride was 100 mol %, and 70.4 mol % of 1,4-butanediol and 26.3 mol % of tetrahydrofuran were formed based on succinic acid anhydride supplied.

EXAMPLE 4

After gradually adding 0.5 liter of an aqueous solution containing 0.3 mol of copper sulfate (II) and 0.15 mol of copper nitrate (II) at 70° C. under stirring to one liter of solution of 1 mol/l sodium hydroxide, they were maintained at 70° C. for one hour. After filtering the deposition products, they were washed by passing one liter of warmed water at 60° C. After re-dispersing the cake into one liter of water at 60° C., 50 g of commercially available zinc oxide was dispersed and stirred for one hour. After filtering the solid matters, they were washed by passing 5 liter of warmed water at 60° C. The resultant solids were dried for 12 hours while supplying air at 140 C. After pulverizing the dried solids, 10-20 mesh fractions were sieved to obtain 78.5 g of a copper oxide-zinc oxide catalyst. The entire amount of the copper oxide-zinc oxide catalyst was added to a solution of 200 cc of acetone containing 1.53 g of rhenium oxide ($Re_2O_7$) dissolved therein and, while stirring properly, left at a room temperature for one day and one night. Then, it was heated to 80° C. to evaporate and dry-up acetone to solids and further dried in a drier at 120° C. for 12 hours and at 150° C. for 12 hours to prepare a rhenium oxide-copper oxide-zinc oxide catalyst. The content of rhenium and copper, as the metal component in the resultant catalyst were 1.5% by weight and 35% by weight respectively.

Using 15 cc of the catalyst prepared as described above, the catalyst reduction treatment and 1,4-butanediol production were carried out in the same procedures as those in Example 2.

As a result, the conversion of maleic acid anhydride was 100 mol %, and 90.2 mol % and 1,4-butanediol and 2.5 mol % of tetrahydrofuran were formed based on maleic acid anhydride supplied. Succinic acid anhydride was not detected in the product.

EXAMPLE 5

Using the reduction catalyst employed in Example 4, a gas mixture of maleic acid anhydride and hydrogen (1:600 molar ratio) was caused to pass without using a solvent under the condition at 220° C., under 40 kg/cm$^2$G and at G.H.S.V. of 4,400 hr$^{-1}$.

As a result, the conversion of maleic acid anhydride was 100 mol %, and 76.5 mol % of 1,4-butanediol and 1.8 mol % of tetrahydrofuran were formed based on maleic acid anhydride supplied. Succinic acid anhydride was not detected in the product.

EXAMPLE 6

Using the reduction catalyst employed in Example 4, a solution of maleic acid anhydride in 1,4-dioxane (maleic acid anhydride/1,4-dioxane=1/4 molar ratio) and hydrogen were caused to pass at a ratio) and hydrogen were caused to pass at a ratio of 800 mol of hydrogen based on one mol of maleic acid anhydride under the conditions at 220° C., under an elevated pressure of 60 kg/cm$^2$G and at G.H.S.V. of 3,800 hr$^{-1}$.

As a result, the conversion of maleic acid anhydride was 100 mol %, and 82.3 mol % of 1,4-butanediol and 2.1 mol % of tetrahydrofuran were formed based on maleic acid anhydride supplied. Succinic acid anhydride was not detected in the product.

COMPARATIVE EXAMPLE 1

A rhenium oxide-zinc oxide catalyst was prepared in the same procedures as those in Example 1 except for using a zinc oxide catalyst (trade name: G-72, manufactured by Nissan Gardler Co.) instead of the copper oxide-zinc oxide catalyst (trade name: N-211, manufactured by Nikki Kagaku Co.). The rhenium content, as the metal component, in the resultant catalyst was 1.5% by weight.

The catalyst reduction treatment and the 1,4-butanediol production were conducted in the same procedures as those in Example 1 using 15 cc of the catalyst prepared as described above.

As a result, the conversion of maleic acid anhydride was 25.6 mol %, and 1,4-butanediol was not formed, except 1.97 mol % of succinic acid anhydride and 1.3 mol % of tetrahydrofuran based on maleic acid anhydride supplied. Other products than succinic acid anhydride and tetrahydrofuran were n-butanol, etc.

COMPARATIVE EXAMPLE 2

The catalyst reduction treatment and the production of 1,4-butanediol were conducted in the same procedures as those in Example 1 except for using 15 cc of a commercially available copper oxide-zinc oxide catalyst with the copper oxide/zinc oxide weight ratio of 50/45 (trade name: N-211, manufactured by Nikki Kagaku Co.)

As a result, the conversion of maleic acid anhydride was 100 mol %, and 16.4 mol % of 1,4-butanediol and 8.5 mol % of tetrahydrofuran were formed based on maleic acid anhydride supplied. Other products were γ-butyrolactone, n-butanol, etc. Succinic acid anhydride was not detected in the product.

What is claimed is:

1. A process of producing 1,4-butanediol comprising: hydrogenating a compound selected from the group consisting of maleic acid, anhydride, succinic acid anhydride and mixtures thereof in a gas phase and in the presence of a catalyst comprising rhenium, copper, and zinc.

2. The process recited in claim 1 wherein said catalyst comprises rhenium oxide, copper oxide, and zinc oxide.

3. The process recited in claim 2 wherein said compound is contained in a solvent.

4. The process recited in claim 3 wherein said compound maleic acid anhydride.

* * * * *